United States Patent [19]

Gilstad et al.

[11] Patent Number: 4,852,579
[45] Date of Patent: Aug. 1, 1989

[54] PHOTOCHARACTERIZATION AND TREATMENT OF NORMAL ABNORMAL AND ECTOPIC ENDOMETRIUM

[75] Inventors: Dennis W. Gilstad; Ronald L. Branstetter; Ralph H. Hill, Jr., all of San Antonio, Tex.

[73] Assignee: Karl Storz Endoscopy GmbH and Company, Fed. Rep. of Germany

[21] Appl. No.: 40,597

[22] Filed: Apr. 20, 1987

[51] Int. Cl.⁴ .............................................. A61B 5/02
[52] U.S. Cl. ................................ 128/665; 250/461.2; 250/483.1
[58] Field of Search ................. 128/6, 303.1, 665, 633, 128/653; 250/461.2, 483.1

[56] References Cited

U.S. PATENT DOCUMENTS 4,675,529  6/1987  Kushida .................... 128/665 X

FOREIGN PATENT DOCUMENTS 2126717  3/1984  United Kingdom ............... 128/633

Primary Examiner—William E. Wayner
Attorney, Agent, or Firm—Matthews & Branscomb

[57] ABSTRACT

A method and apparatus for optical diagnosis and treatment of abnormal cells through the use of hormone-specific chemical markers which are preferential to genital tissues. Abnormal cells can be differentiated from normal cells by the amount of fluorescent or thermal radiation produced by the chemical marker retained in the respective cells when irradiated with electromagnetic radiation at a predetermined wavelength. Once the abnormal cells have been detected, they can be treated through the use of an optical technique based on photochemical or thermal reactions which can be controlled to destroy the abnormal cells, while leaving normal cells unharmed.

10 Claims, 6 Drawing Sheets

4,852,579

PHOTOCHARACTERIZATION AND TREATMENT OF NORMAL ABNORMAL AND ECTOPIC ENDOMETRIUM

FIELD OF THE INVENTION

The present invention relates to an optical technique for differentiating normal and abnormal endometrium from other tissue. In particular, the present invention can be used to differentiate endometriotic sites from surrounding tissue, as well as differentiating hyperplasia of the endometrium and adenocarcinoma from normal endometrium. Furthermore, the present invention provides an optical technique which can be used to destroy the undesirable tissue immediately after identification.

BACKGROUND

Endometriosis is the occurrence of endometrial tissue in places other than the uterus. This condition is associated with pelvic pain, infertility, and excessive bleeding during menstruation. Endometriosis is generally diagnosed by a visual inspection of the peritoneal cavity. However, there is growing evidence that simple visual inspection of the peritoneal cavity is a poor technique for the diagnosis of endometriosis, especially since many of the lesions are microscopic in size.

Recently, a diagnostic technique has been developed for the use of hematoporphyrin-derivatives (HPD), drugs which concentrate in cancer cells. Because this drug is selectively retained by proliferating tissues, it can be used as a "tumor-specific" marker. When tissue is irradiated with light having a wavelength of approximately 405 nanometers, cells containing HPD produce fluorescent radiation, which can be used to assist the physician in locating cancerous tissue. In addition, HPD has a cytotoxic effect by inducing the release of an oxygen singlet when the cells are irradiated with light in the wavelength range of 630 nm. This latter phenomenon can be used in the treatment of the cancerous tissue. The HPD diagnostic and treatment technique employing multiple radiation sources is shown generally in U.S. Pat. Nos. 4,541,438; 4,576,173; and 4,592,361 issued to Parker. In addition, U.S. Pat. No. 4,336,809, issued to Clark, shows the use of a single laser, which produces light at two wavelengths, as the energy source for both the diagnosis and treatment of HPD-marked cells.

Despite its utility for locating cancerous cells, the HPD diagnostic technique has a number of problems. For example, the timing between the administration of the drug and the diagnosis is critical (approximately 48 hours). In addition, the HPD makes the patient photosensitive, thus creating a risk of possible phototoxic side effects. For example, photosensitizers such as HPD are capable of intra-ocular penetration through the blood aqueous and blood-retina barrier and may subsequently degrade the ocular lens and retina on exposure to ultraviolet light (200-400 nm). Therefore, patients undergoing HPD diagnostic treatments usually must be isolated for several days in a dark room to prevent undesired photosensitivity reactions.

SUMMARY OF THE INVENTION

The present invention overcomes the difficulties of the prior art by providing an optical diagnosis and treatment technique which avoids the use of porphyrin-based chemical markers which cause undesired photosensitivity reactions. Specifically, the present invention discloses a method for detecting and treating abnormal cells through the use of a non-porphyrin chemical marker which is preferential to genital tissues. In the preferred embodiment, the chemical marker is chosen from a group of hormone analogs including tamoxifen citrate, clomiphene, and danazol.

In addition to overcoming the difficulties related to HPD chemical markers, the present invention discloses an effective optical technique which provides the physician with a real-time visualization of the abnormal cells to ensure proper diagnosis of the condition. The real-time feature of the present invention is accomplished through the use of either laser induced-fluorescence thermal imaging, or a combination of fluorescence and thermal imaging.

The first technique involves the use of a laser with a chopped white light source to obtain alternate white light and fluorescent images. Digital image processing is then used with rapid-sequence exposures to produce distinct composite images having normal backgrounds.

An alternate method of abnormal cell detection is based on the principles of thermal imaging. If chemically enhanced abnormal cells and normal cells are excited by the proper wavelength of light, more energy will be absorbed and converted to thermal energy by the enhanced cells than by the unenhanced cells. As a result, the enhanced cells will be at a higher temperature after the excitation. An image from an infrared camera allows the physician to differentiate between the relatively warmer and cooler portions of the tissue to diagnose the existence of abnormal cells.

As a third embodiment, the invention system can be modified to combine the thermal and fluorescent images to obtain a composite white light, fluorescent, and a thermal image. Since the fluorescent emissions are typically at a very low intensity, the information provided by the thermal image can be combined with the fluorescent signal to enhance the detection of the abnormal cells.

The principles outlined above with regard to detection of abnormal cells are also used for the treatment of the abnormal cells. Treatment can be based on the photochemical reactions and/or temperature rise due to absorbed energy. The longer the tissue is irradiated, the greater the temperature difference between the normal cells and the abnormal cells. By controlling the photochemical or thermal reaction, the abnormal cell is destroyed while leaving the normal cell unharmed.

DETAILED DESCRIPTION OF THE PREFERRED EMBODIMENT

Figure 1:
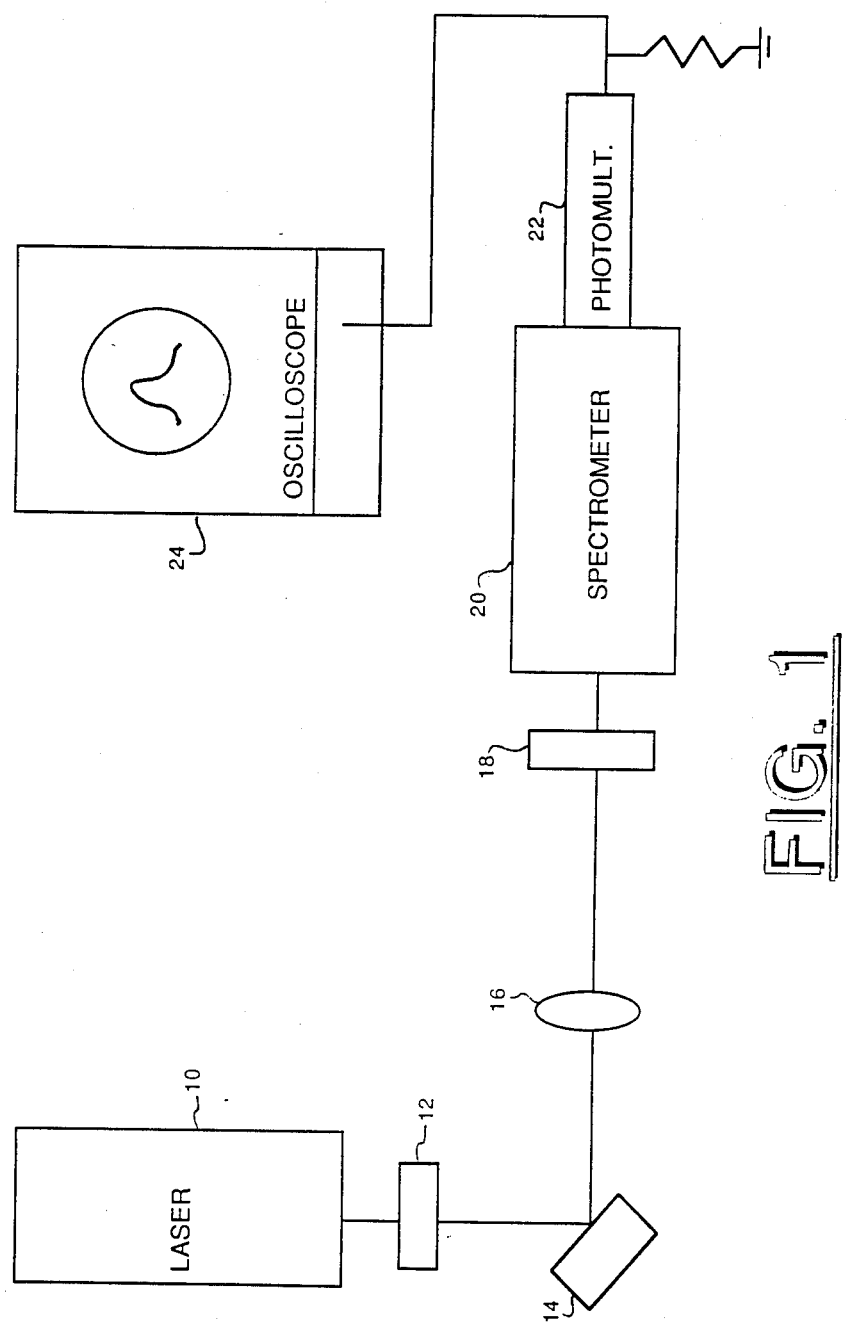
FIG. 1 is a schematic representation of the system configuration of the present invention for measuring total fluorescence as a function of dose level.
Figure 2:
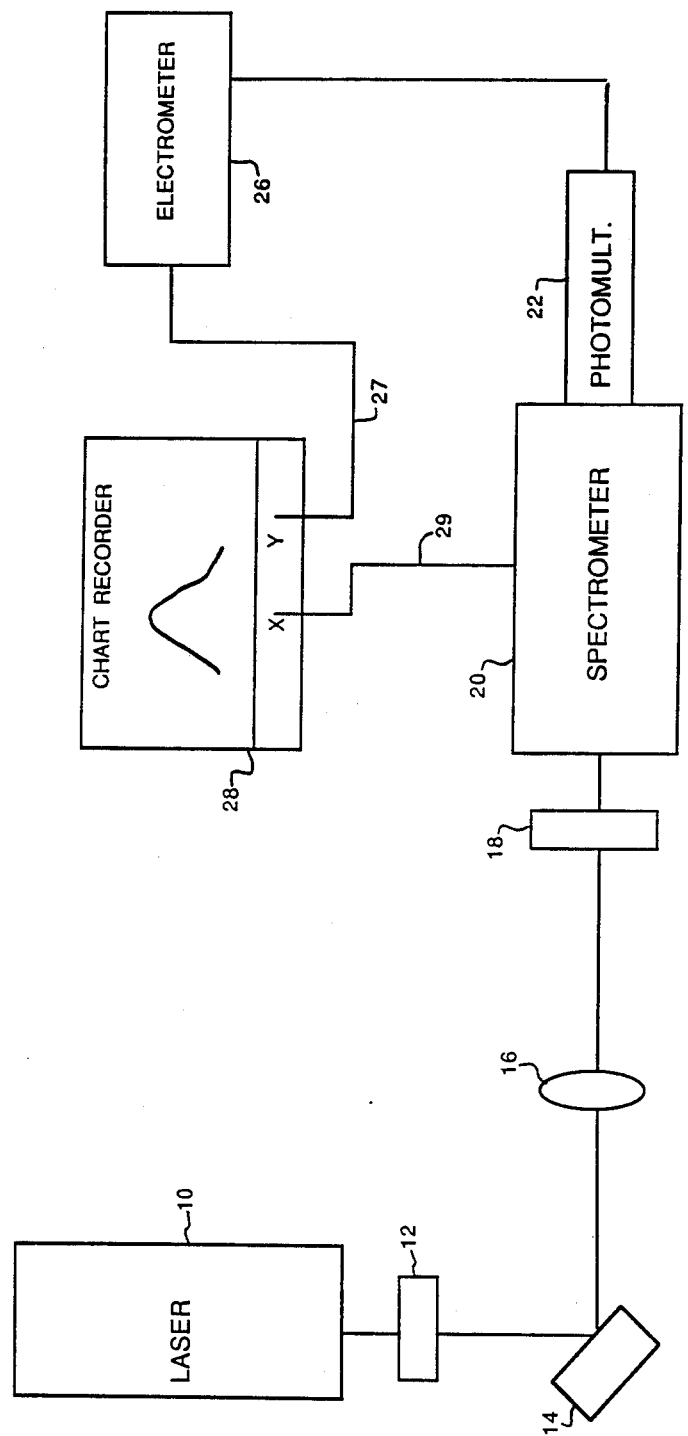
FIG. 2 is a block diagram showing the major system components used in the present invention for measuring laser-induced fluorescence as a function of wavelength.
Figure 3:
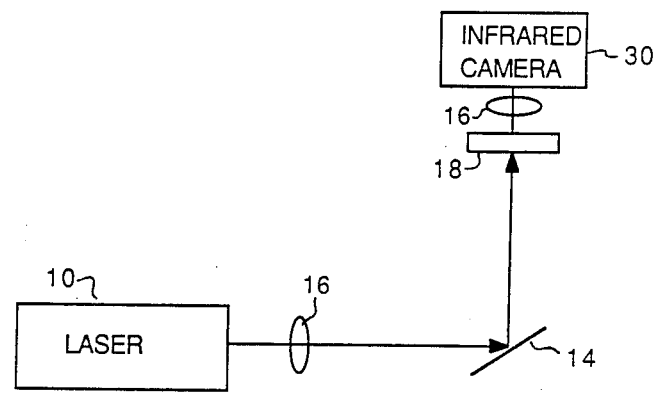
FIG. 3 is a block diagram of the major system components of the preferred embodiment for the combined use of fluorescent and conventional imaging of abnormal cells.
Figure 4:
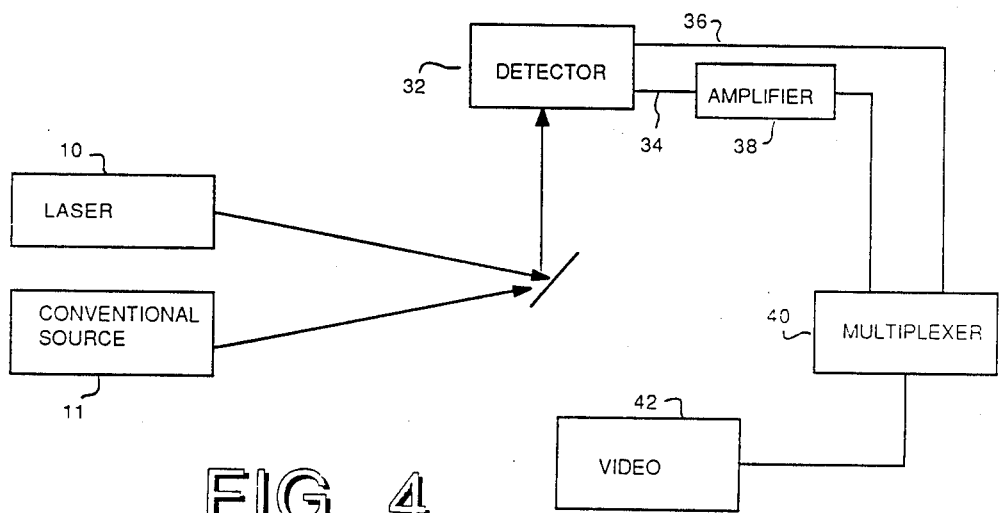
FIG. 4 is a block diagram showing the major system components used in the thermal imaging embodiment of the present invention.

The system components of the various embodiments of the present invention are shown generally in FIGS. 1 through 4. FIGS. 1 and 2 illustrate the system configuration of the preferred embodiment for the use of laser-induced fluorescence. FIG. 3 is a schematic block diagram of the system components of the preferred embodiment for diagnosis of abnormal cells using a combination of laser-induced fluorescence and conventional imaging techniques. Each of these systems will be discussed in greater detail below in connection with the theoretical basis for the operation of the specific configurations. FIG. 4 is system block diagram of the preferred embodiment of the system components for diagnosis and treatment of abnormal cells by thermal imaging techniques.

As was discussed above, the diagnostic system of the present invention is based on the use of hormone analog chemical markers. FIG. 1 is a schematic block diagram of the system used to make an initial determination of the fluorescence versus dose characteristics of the chemical marker. For determination of the fluorescence characteristics, light from an excitation source 10 is passed through a shutter 12 to illuminate the specimen of material 14. In the preferred embodiment, the excitation source is a laser producing light at a specific wavelength to cause fluorescence. The shutter 12 of the system shown in FIG. 1 can be eliminated if a pulsed laser is used. In the preferred embodiment, the excitation light is transmitted to the specimen and the fluorescent light is returned via a fiber optic delivery system used in conjunction with an endoscope. The use of such a fiber optic endoscopic system is described generally in U.S. Pat. No. 4,072,147.

The fluorescence characteristics of the material are determined by analysis of the reradiated light which passes through lens 16 and filter 18. The filter 18 can be selected to minimize scattered light from the laser 10. The spectrometer 20 disperses the light which is then detected by the photomultiplier 22 and amplified to provide input for a suitable display device, such as the oscilloscope 24 shown in FIG. 1.

The system shown in FIG. 2 for measuring intensity as a function of wavelength comprises many of the elements shown in FIG. 1; however, the output of the photomultiplier tube is fed into an electrometer 26 which provides a fluorescence amplitude signal, illustrated by line 27, for input into the chart recorder 28. Wavelength information is provided to the chart recorder by line 29.

Laser-induced fluorescence is the emission of light resulting from the absorption of laser light by a substance. The wavelength of the reradiated light contains a major portion at the wavelength of the exciting laser light. However, it also contains many new wavelength components which are determined by the molecular structure of the absorbing material. Luminescence is a general term used to encompass the concepts of fluorescence and phosphorescence. The distinction between the two types of light emissions is that fluorescence may appear within a few nanoseconds, while phosphorescence may appear on time scales as long as seconds. Fluorescence is characterized by two spectra. A fluorescent molecule emits a fluorescence spectrum after it absorbs radiation within an excitation spectrum. The spectral distribution of the fluorescent radiation is a physical and absolute characteristic of a given substance for a given wavelength and is useful for qualitative considerations. The emission intensity of fluorescence at a given wavelength is useful for quantitative analysis with a given instrument, after standardization.

The laser generates a light beam having an extremely narrow spectral bandwidth. As a consequence, the incident laser light does not mask the emitted fluorescence. Nonetheless, the viewing environment must still be "dark" since normal daylight will mask the fluorescence. In addition, the high energy generated by the laser will produce fluorescent signals which otherwise would be so weak that they could not be measured, or "seen."

One would not normally think of human tissue as a fluorescent material, because when observed under standard room light conditions, the dominant processes are light scattering and absorption. The wavelength dependence of these processes gives the tissue its characteristic color. Each photon from the room light is either scattered or absorbed by the tissue, but its wavelength remains the same. A very slight shift in wavelength may, in fact occur, e.g. Raman shifts, but it is so small that it can be neglected for the present discussion. Since room light contains all visible wavelengths at a far higher density than the fluorescent light, the latter will be masked.

Mentioning fluorescence in medicine brings to mind the well-known Wood lamp for diagnosis of mycotic infections. In fact, quite a number of cells will produce fluorescence when illuminated with conventional ultraviolet light. Tissue may produce fluorescence when illuminated with longer wavelengths, but it is masked by the incident light which typically has a photodensity factor $10^6$ higher. This phenomenon is well illustrated by the common phosphorescent watch dial, which the casual observer believes to only "fluoresce" in the dark. The dial is constantly emitting phosphorescent radiation, but this radiation can only be seen in the dark.

Figure 5:
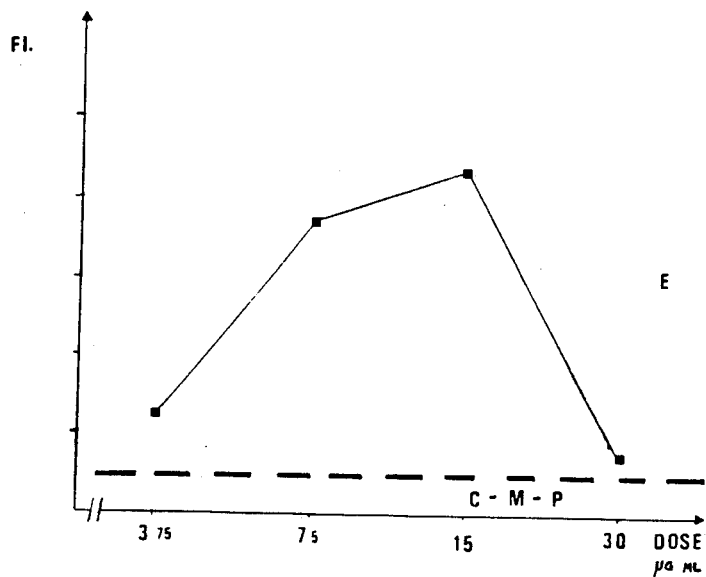
FIG. 5 is a graphical illustration of fluorescent intensity versus dose level for homogenized enhanced tissue incubated with tamoxifen citrate.
Figure 6:
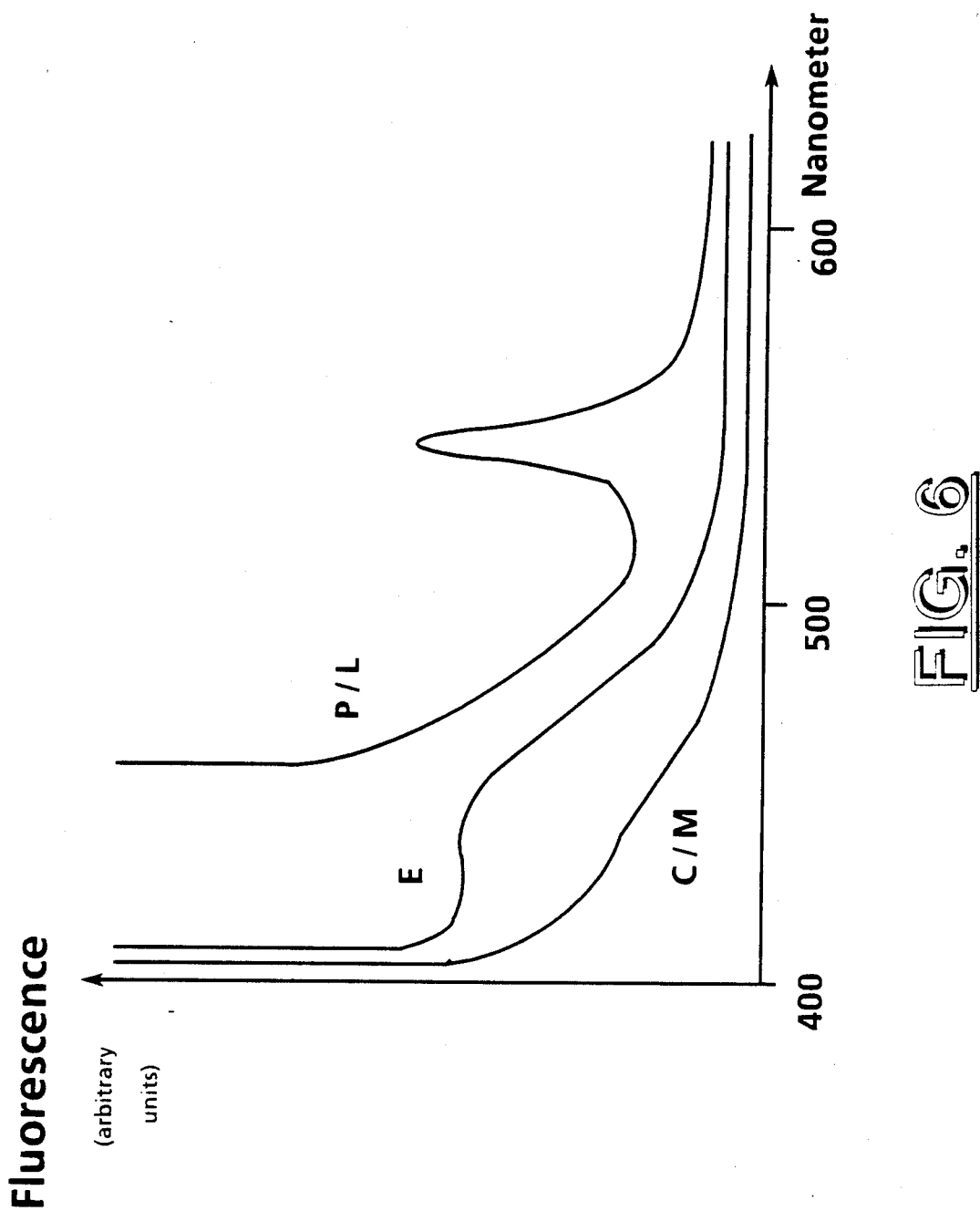
FIG. 6 is a graphical illustration of fluorescent intensity versus wavelength for unenhanced homogenized tissue irradiated with light having a wavelength of 396 nm.
Figure 7:
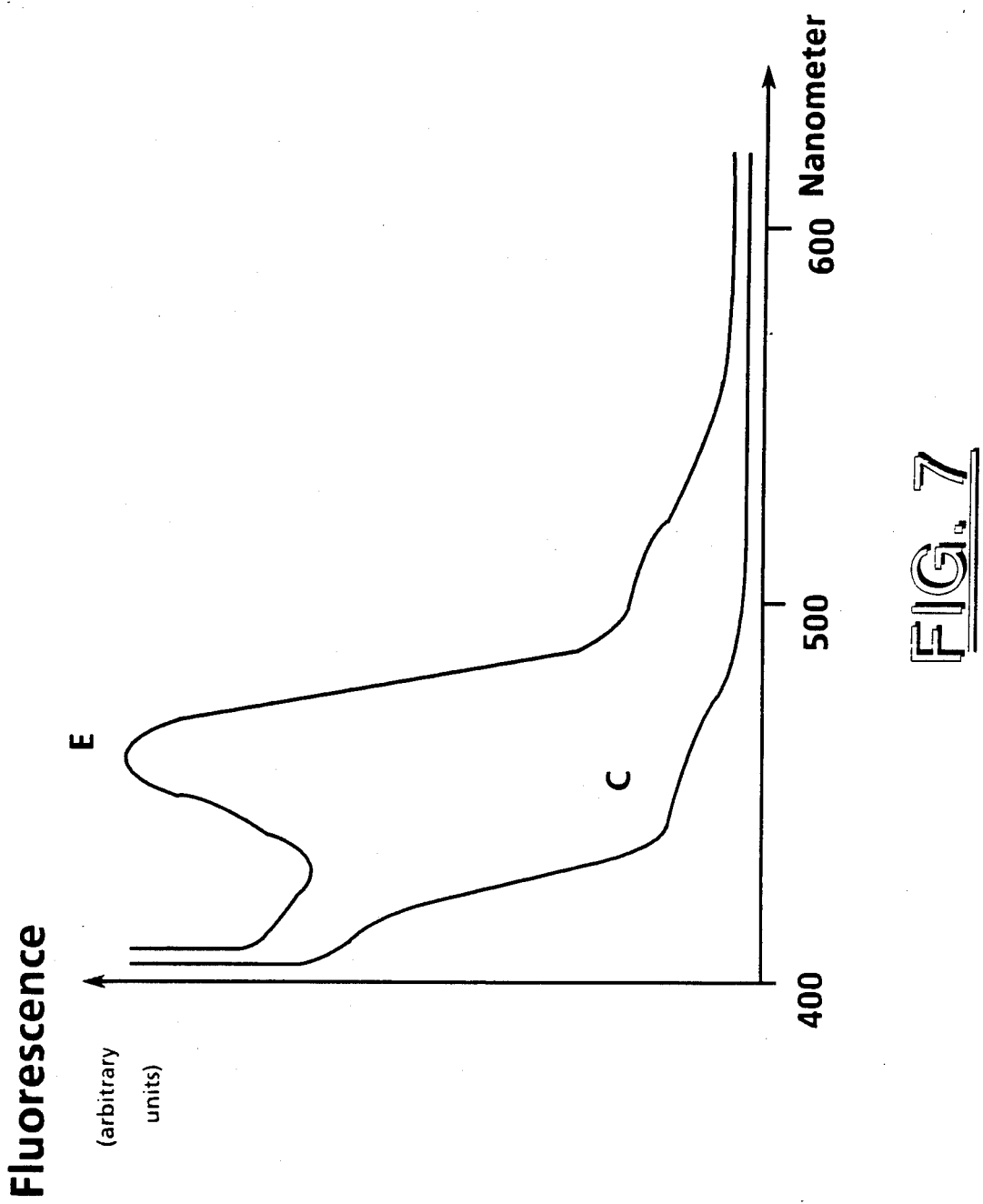
FIG. 7 is a graphical illustration of fluorescent intensity versus wavelength for homogenized enhanced tissue incubated with tamoxifen citrate and irradiated with light having a wavelength of 340 nm.

The principles discussed above were demonstrated by measuring the fluorescence characteristics of unenhanced homogenized tissues (used as control) and homogenized tissues enhanced with chemical markers. Homogenized tissues were used rather than larger tissue pieces to avoid the geometrical interference caused by such larger pieces. FIGS. 5 through 7 are graphical illustrations of typical data obtained during these measurements. FIG. 5 is a graphical representation of the dose response curve for a sample of tissue homogenate incubated with tamoxifen citrate. The data shown in this figure was obtained by exposing the tissue homogenate to excitation radiation having a wavelength of 340 nm. As can be seen, the endometriotic tissue E exhibits significant fluorescence, while the signals emitted by the control endometrium, myometrium, and peritoneum are well below the sensitivity limits of the instrumentation, shown by the dashed line C-M-P.

The graphical illustrations discussed above indicate that endometriotic tissue enhanced with hormone-analog chemical markers can be differentiated from other tissues through the use of laser-induced fluorescence measurement techniques. FIGS. 6 and 7 further demonstrate the use of laser-induced fluorescence principles as a diagnostic technique based on the system configuration discussed above in connection with FIG. 2.

FIG. 6 is a graphical representation of a typical fluorescence spectrum of unenhanced tissue homogenate exposed to excitation radiation having a wavelength of 396 nm. The curve P/L represents the fluorescence characteristics of the peritoneum and corpus luteum and the curve C/M represents the fluorescence characteristics of the control endometrium and myometrium. The curve E represents the fluorescence characteristics of the endometriosis. As can be seen in FIG. 6, the endometriosis has a different fluorescence response than the control endometrium and myometrium in the range from approximately 425 to 450 nm. In theory, these results suggest that endometriosis can be detected without the use of chemical enhancers if extremely accurate and sensitive instrumentation is used for the measurement. In practice, however, the intensity differential shown in FIG. 6 is virtually impossible to use as a basis for differentiating endometriosis from normal endometrium.

In FIG. 7, the fluorescence spectrum is shown for tissue homogenate enhanced with tamoxifen citrate and exposed to excitation radiation having a wavelength of 340 nm. As was discussed above, Tamoxifen is a hormone-analog chemical marker which is preferential to genital tissues. The fluorescent intensity of the enhanced endometriotic tissue E differs from that of the control endometrium C over the majority of the measured spectrum and exhibits a peak at approximately 450 nm. This peak and the substantial difference in fluorescent intensity can be used to identify endometriotic sites.

One of the difficulties with the use of laser-induced fluorescence inspection methods in conjunction with endoscopy is the very weak signal produced. When only one light source is used to produce the fluorescence, the observer tends to lose his landmark needed for exact orientation. To overcome this difficulty, an alternate embodiment of the invention provides a system wherein the tissue is illuminated alternately with a conventional light source and the laser light. This sequence of illumination, therefore, produces two images which must be combined.

The human eye normally has a good "memory" for any given observed image. Therefore, when images are produced in a very rapid sequence, an individual is normally able to combine them to obtain a composite image. However, in the present example, there is a substantial difference in the intensity of the two images. In general, fluorescent light has a photodensity approximately one million times less than the excitation source. The human eye is unable to compensate for differences of this magnitude. Therefore, it is not possible to obtain the composite normally obtained by viewing the images in sequence.

One solution to the difficulties discussed above is to replace the human eye with electronic amplifiers and a video camera. By transforming the light into an electric signal, the problems associated with modulation are simplified. The two images can be combined on a single screen with sufficient enhancement of the low energy image. The use of such an electronic system thus allows a "combined image" to be constructed in a very short period of time, avoiding the necessity of the examiner having to hold an endoscope for extended periods.

The system for combining the images in the manner described above is shown generally in FIG. 3. In this system, the tissue 14 is alternately illuminated with light from the laser 10 and the conventional light source or other lasers 11. The resulting images are detected by a detector 32 which produces electrical output signals corresponding to the image produced by the laser 10 and the conventional source 11. These signals are represented by signal lines 34 and 36, respectively. The fluorescent signal resulting from the laser excitation is amplified by an amplifier 38. The amplified fluorescent signal and the conventional signal are combined in a multiplexer circuit 40 and displayed on an appropriate video device 42 to produce the desired composite image.

One of the novel features of the system described above is the superposition of successive images from the two light sources to produce a composite image. Synchronization of the images produced by the two light sources allows the construction of a composite image which is in "real time." The human eye accepts as "real time" the successive reproduction of 23 frames per second. Therefore, there is a time window of approximately 44 milliseconds for the electronic composition of a single frame of the combined image.

An alternate method of abnormal cell detection is based on the principles of thermal imaging using the system shown in FIG. 4. If tissue containing enhanced abnormal cells and normal cells is excited by the proper wavelength of light, more energy will be absorbed and converted to thermal energy by the enhanced cells than by the unenhanced cells. As a result, the enhanced cells will be at a higher temperature after the excitation. An image from a infrared camera 30 will allow the physician to differentiate between the relatively warmer and cooler portions of the tissue to diagnose the existence of abnormal cells.

As a third embodiment, the system of the present invention can be modified to combine the thermal and fluorescent images to obtain a composite white light, fluorescent, and a thermal image. Since the fluorescent emissions are typically at a very low intensity, the information provided by the thermal image can be combined with the fluorescent signal to enhance the detection of the abnormal cells. When the thermal and fluorescent images are used in combination, one chemical enhancer is used to provide optimum fluorescence, while a second enhancer can be used to provide optimum thermal absorption.

The principles outlined above with regard to detection of abnormal cells can also be used for the treatment of the abnormal cells. Treatment can be based on either photochemical reactions and/or temperature rise due to absorbed energy. Both of these phenomena can occur simultaneously. The abnormal cells can be treated with one enhancer which works well with photochemical reactions or with a second enhancer which creates a temperature rise. By controlling the photochemical or thermal reaction, the diseased cell can be destroyed while leaving the normal cell unharmed.

Although the method and apparatus of the present invention has been described in connection with the preferred embodiment, it is not intended to be limited to the specific, form set forth herein, but, on the contrary, it is intended to cover such alternatives and equivalents as can reasonably be included within the spirit and scope of the invention as defined by the appended claims.

We claim:

1. A method of photocharacterization of tissue, comprising the steps of:
   injecting said patient with a hormone-specific chemical marker, said chemical marker being preferential to genital tissue;
   illuminating a portion of said tissue with an optical excitation means producing light having a predetermined wavelength; and
   detecting fluorescent radiation produced by said portion of tissue; and
   correlating said fluorescent radiation with the existence of abnormal cells in said portion of tissue.

2. The method according to claim 1, wherein said optical excitation means further comprises an optical delivery guide means for selectively radiating said portion of tissue with said light and an optical return guide means for collecting fluorescent radiation produced by said tissue.

3. The method according to claim 2, said optical delivery means and said optical return guide means comprising an endoscope.

4. The method according to claim 3, said optical excitation means comprising a laser.

5. The method according to claim 4, said chemical marker being preferential to the genital tissues.

6. The method according to claim 5, said chemical marker being chosen from the group consisting of tamoxifen citrate, clomiphene, and danazol.

7. A method for photocharacterization of tissue wherein said tissue has absorbed a hormone-specific chemical marker, comprising the steps of:
   irradiating a portion of said tissue with a source of laser light having a predetermined wavelength;
   irradiating said portion of said tissue with conventional light;
   detecting fluorescent radiation produced by said tissue in response to said laser light;
   processing said fluorescent radiation to obtain a first image at a first intensity;
   detecting light reflected by said portion of tissue in response to said conventional light;
   processing said reflected light to obtain a second image at a second intensity;
   amplifying said first image at said first intensity to obtain a first image having approximately the same intensity as said second image;
   combining said first and second images to obtain a composite image; and
   correlating said composite image with the existence of abnormal cells in said portion of tissue.

8. The method according to claim 7, said step of correlating said composite image further comprising the step of projecting said first and second images on a video screen.

9. The apparatus according to claim 8, said chemical marker being preferential to the genital tissues.

10. The method according to claim 9, said chemical marker being chosen from the group consisting of tamoxifen citrate, clomiphene, and danazol.

* * * * *